United States Patent [19]

Chiodini et al.

[11] Patent Number: 4,882,315
[45] Date of Patent: Nov. 21, 1989

[54] AMINOGLYCOSIDE STEROIDS, A PROCESS FOR THEIR PREPARATION, THEIR USE AND PHARMACEUTICAL COMPOSITIONS CONTAINING THEM

[75] Inventors: Laura Chiodini, Busto Arsizio; Mauro Gobbini, Sesto Calende; Sergio Mantegani, Milan; Daniel Ruggieri, Milan; Aldemio Temperilli, Milan; Gabriella Traquandi, Cornate d'Adda; Patrizia Ferrari, Varese, all of Italy

[73] Assignee: Farmitalia Carlo Erba S.p.A., Milan, Italy

[21] Appl. No.: 133,035

[22] PCT Filed: Jan. 7, 1987

[86] PCT No.: PCT/EP87/00004
§ 371 Date: Oct. 29, 1987
§ 102(e) Date: Oct. 29, 1987

[87] PCT Pub. No.: WO87/04167
PCT Pub. Date: Jul. 16, 1987

[30] Foreign Application Priority Data

Jan. 9, 1986 [GB] United Kingdom ............... 8600489

[51] Int. Cl.⁴ .................................. A61K 31/58
[52] U.S. Cl. ................................ 514/26; 514/172; 536/5; 536/6; 536/6.1; 540/90
[58] Field of Search ............ 536/5, 6, 6.1; 514/182, 514/172, 26; 260/397.5; 540/90

[56] References Cited

PUBLICATIONS

"Side Reactions During Saponification of Acyl Cardenolides with $NH_3$", Makarevich et al., (1984), Chem. Ass. 102: 185349.

"Zur Stereochemie der Epoxycardanolide (Isogenine)", Krass et al., Helvetica. Chem. Acta. 55(5), 1352–1371.

"Synthesis of Isobufalin Methyl Ester", J.C.S.(CC), 1967, 644–646, Kasturi et al., (1967).

"Inhibition of Potentiation of Ovabain Inotropism by Modified Cardenolides", Davisson et al., (1972), Chem. Asst. 78: 119146.

Primary Examiner—H. M. S. Sneed
Assistant Examiner—J. Saba
Attorney, Agent, or Firm—Brooks Haidt Haffner & Delahunty

[57] ABSTRACT

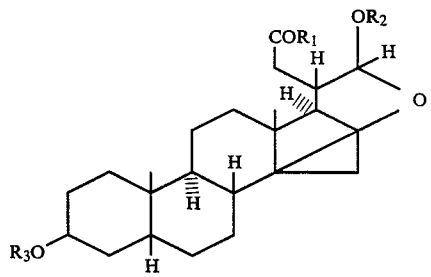

Compounds I (either $R_1=OH$, $C_1-C_4$ alkoxy and $R_2=H$, $C_1-C_4$ alkyl, or $R_1+R_2=$ a chemical bond; $R_3=$ an aminodeoxy or aminodideoxy or aminotrideoxy sugar residue of the D and L series, the glycosidic linkage being $\alpha$ or $\beta$) and their pharmaceutically acceptable salts are useful as antihypertensive agents. Their preparation and use as well as pharmaceutical compositions containing them are also described.

7 Claims, No Drawings

AMINOGLYCOSIDE STEROIDS, A PROCESS FOR THEIR PREPARATION, THEIR USE AND PHARMACEUTICAL COMPOSITIONS CONTAINING THEM

The invention relates to aminoglycoside steroids, to a process for their preparation and to pharmaceutical compositions containing them.

The invention provides aminoglycoside steroids having the general formula I

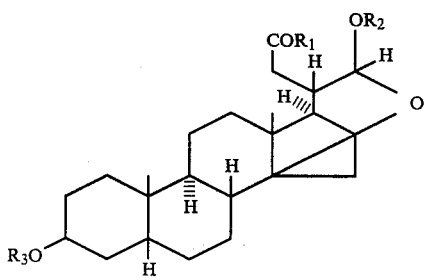

wherein either $R_1$ represents a hydroxy group or an alkoxy group having from 1 to 4 carbon atoms and $R_2$ represents a hydrogen atom or an alkyl group having from 1 to 4 carbon atoms, or $R_1$ and $R_2$ taken together represent a chemical bond; and $R_3$ represents an optionally alkyl-substituted-aminodeoxy- or aminodideoxy- or aminotrideoxy-sugar residue of the D or L series. Such sugar residues are, for example, 2-amino or 2-alkylamino-2-deoxy-hexoypyranosyl, 3-amino or 3-alkylamino-3-deoxy-hexopyranosyl, 3-amino or 3-alkylamino-3,6-dideoxy-hexopyranosyl, 3-amino or 3-alkylamino-2,3,6-trideoxy-hexopyranosyl and 4-amino or 4-alkylamino-2,4,6-trideoxy-hexopyranozyl residues of the D and L series.

The optional alkyl substituent(s) of the sugar residue are preferably lower alkyl with $C_1$–$C_4$ atoms, e.g. methyl, ethyl, propyl and butyl. Advantageously the alkyl radicals may substitute the amino group of the sugar residue.

The glycosidic linkage can be $\alpha$ or $\beta$. An alkoxy group may be methoxy, ethoxy, propoxy or butoxy group. An alkyl group may be methyl, ethyl, propyl or butyl group. Pharmaceutically acceptable salts of the compounds of the general formula I are also provided by the invention.

"Pharmaceutically acceptable salts" refers to those salts which retain the biological effectiveness and properties of the free bases and which are not biologically or otherwise undesirable. Such salts are formed with inorganic acids such as hydrochloric, hydrobromic, sulfuric, nitric or phosphoric acid and organic acids such as acetic, propionic, glycolic, pyruvic, oxalic, malic, malonic, succinic, maleic, fumaric, tartaric, citric, benzoic, cinnamic, mandelic, methanesulfonic, ethanesulfonic, p-toluene sulfonic or salicylic acid.

The invention further provides a process for the preparation of the aminoglycoside steroids of the general formula I as herein defined, which process comprising condensing a steroid having the formula II

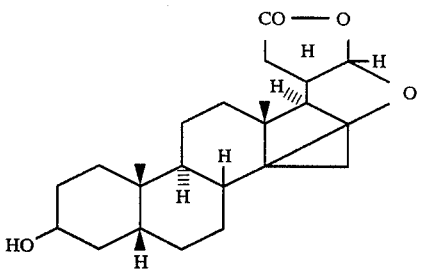

with a protected 1-halo derivative of an aminodeoxy, aminodideoxy or aminotrideoxy sugar of the D or L series and removing the protecting groups from the resultant compound. This can preferably be effected with a base. The condensation is desirably carried out in a suitable organic solvent in the presence of silver catalyst. The use of silver trifluoromethanesulphonate as catalyst, preferably under conditions described in US 4112076 of the applicant, is especially advantageous.

The base desirably used to remove the protecting groups may be a hydroxide or methoxide of sodium, potassium or of barium or may be triethylamine. The reaction may be performed at room temperature over a period of from some hours to several days. This operation generally gives compounds of the general formula I wherein $R_1$ is a hydroxy or alkoxy group and $R_2$ is a hydrogen atom or alkyl group. These compounds may be converted by cyclization into the compounds of the general formula I wherein $R_1$ and $R_2$ together represent a chemical bond, forming a lactone ring.

The cyclization may be carried out in hydrochloric acid at room temperature and pH 1–2 for, e.g. from three to five hours. The steroids of the formula II and the aminodeoxy, aminodideoxy and aminotrideoxy sugars used as starting materials are well known compounds or may be prepared by methods well known in the art.

The aminoglycoside steroids according to the invention and their pharmaceutically acceptable salts are capable of inhibiting specific ouabain binding without inhibiting $Na^+$, $K^+$-ATPase activity and thus they may be useful in pharmaceutical compositions. They can also be used in the making of a medicament for the treatment of hypertension.

'In vitro' assays to test the ability of aminoglycoside steroids of formula I to displace specific ouabain binding to the $(Na^+K^+)$-AtPas receptors without inhibiting the $(Na^+—K^+)$-ATPase enzymatic activity.

Radiochemical assay:

A microsomial fraction enriched in $(Na^+—K^+)$-ATPase was prepared from dog kidney outer medulla, according to Jorgensen (BBA 356: 36–52, 1974).

The partially purified enzyme (0.5 μg of protein) was incubated in 3 mM $MgCl_2$, 3 mM EGTA, 80 mM Hepes buffer (pH 7.4) and 2 mM $y^2-P^{32}$-ATP, final volume 110 μl, at 37° C. for 15 minutes with increasing concentrations of ouabain (a reference compound) or aminoglycoside steroids.

The reaction was stopped by the addition of 0.1 mM of cold perchloric acid (10% final concentration) and 0.5 ml of charcoal suspension (20% w/v). The suspension was centrifuged and the content of $^{32}P$ in the supernatant was measured by liquid scintillation counting. (ref. Mall F. et al.: Biochem Pharm. 33: N.1, 47–53, 1984).

The effects of various concentrations of aminoglycoside steroids and ouabain were expressed as a percentage of the total (Na$^+$—K$^+$)-ATPase activity and IC$_{50}$ values were calculated.

The compounds of the formula I are inactive in this test.

Displacement of ouabain (H$^3$) binding from human red blood cells

The procedure has been described elsewhere (Erdmann E. et al.; Arzneim. Forsh 34(II), no. 10: 1314, 1984).

Washed erythrocytes (about $1-1.8\times10^9$/ml) were incubated in 130 mM NaCl, 1 mM MgCl$_2$, 10 mM glucose, 10 mM sucrose, 10 mM Tris/HCl buffer (pH 7.4) $2\times10^{-9}$M $^3$H ouabain and increasing concentration of the unlabelled aminoglycoside steroids, at 37° C. for 5 hours. Bound oubain was quantitated by a rapid filtration technique (Whatman GF/C glass filter membranes; 'Whatman' is a Trade Mark) to separate free from membrne-bound ouabain. The radioactivity in the filters was determined by liquid scintillation counting. Non specific binding was defined as the binding in the presence of $10^{-3}$M unlabelled ouabain.

The dissociation constant (K$_D$ value) was calculated from the concentration of unlabelled aminoglycoside steroids which inhibit $^3$H-ouabain binding by 50% at equilibrium, by the method of Erdmann et al. (Schmiedeberg's Arch. Pharmacol. 283: 335, 1973). The compounds of this test are effective with a K$_D$ value range of from $10^{-9}$ to $10^{-6}$.

Inhibition of Na$^+$ efflux mediated by the (Na$^+$—K$^+$)-ATPase in human red blood cells The procedure has been described elsewhere (Garay et al., Biochem. Pharmacol. 33: 2013-2020, 1984). Washed red blood cells were suspended to a hematocrit of 20-25% in 74 mM MgCl$_2$, 2 mM KCl, 84 mM sucrose, 10 mM MOPS/Tris buffer (pH 7.4 at 37° C.) and 10 mM glucose.

Red cell suspensions were added in the cold to tubes containing Mg$^{++}$ sucrose-K$^+$ medium with increasing concentration of ouabain and fixed concentrations of aminoglycoside steroids. The tubes were incubated at 37° C. and aliquots of the suspensions were transferred to the cold and spun down at different times (0–10–2–0–30 minutes). External N$^+$ concentrations were measured in the supernatants by atomic absorption. A kinetic analysis of the inhibition of ouabain sensitive Na$^+$ efflux as a function of different aminoglycoside concentrations was done and the IC$_{50}$ for each compound was calculated. The compounds of the formula I are effective in a concentration range of from $10^{-9}$ to $10^{-6}$M.

'In vivo' assays to test the hypotensive activities of aminoglycoside steroids of formula I Indirect measurements of systolic blood pressure was carried out in groups of 4 spontaneously hypertensive rats (SHR,Kyoto), 8 to 10 weeks of age, supplied By Charles Rives, Italy. The animals were maintained in an environment of 36° C. for 10 to 15 minutes to allow pulse pressure to be recorded and then systolic blood pressure and heart rate were measured by the indirect tail cuff method using a W+W, BP recorder, model 8005. The compounds were given orally, suspended in 5% arabic gum, once a day for 4 consecutive days and measurements were carried out before beginning the treatment and 1 and 5 hours after dosing in both the first and fourth day of treatment. Control animals received the vehicle only (0.2 ml/100 g body weight). Drug induced changes in systolic blood pressure were calculated as differences from the pretreatment values.

The formulation of the compounds of the invention as pharmaceutical composition may include solid formulations such as capsules, tablets and powders, or liquid formulations such as elixirs, syrups and suspensions for oral administration. Alternatively, the inventive compounds (I) may be formulated as injections or suppositories.

A carrier and diluent may be included in the pharmaceutical composition which is selected from pulverulent solid carriers such as lactose, saccharose, dextrose, mannitol, sorbitol, cellulose, and glycine etc.

The composition may further contain a lubricant, a binder or a disintegrator. Examples of suitable lubricants are silicon dioxide, talc, magnesium stearate and polyethylene glycol. Examples of suitable binders are starch, gelatin, tragacanth, methyl cellulose and polyvinyl pyrrolidone. Examples of suitable disintegrators are starch and agar etc.

The following Examples illustrate preferred embodiments of the invention.

EXAMPLE 1

3-[(3-amino-3-deoxy-$\beta$-D-glucopyranosyl)oxy]-14,21-epoxy-21-hydroxy-(3$\beta$,5$\beta$,14$\beta$,20S,21R)-24-nor-cholanic acid 374 mg of 3,21-dihydroxy-14,21-epoxy-(3$\beta$,5$\beta$,14$\beta$,20S,21S)-24-nor-cholanic acid lactone dissolved in 80 ml of methylene dichloride were treated dropwise at 0° C. with stirring in presence of 4 g of Molecular Sieves, 4 Å, with a solution of 928 mg of 3-deoxy-2,4,6-tri-O-acetyl-3-trifluoroacetamido-$\alpha$-D-glucopyranosyl bromide in 20 ml of methylene dichloride and a solution of 514 mg of silver trifluoromethanesulfonate in 20 ml of diethyl ether. After 30' at 0° C., the mixture was filtered, the solution washed with a saturated sodium hydrogen carbonate solution, with a saturated sodium chloride solution, dried over anhydrous sodium sulfate and evaporated to dryness. The crude residue was chromatographed on silica gel with toluene-ethyl acetate 4:1 to give 455 mg of 3-[(3-deoxy-2,4,6-tri-O-acetyl-3-trifluoroacetamido-$\alpha$-D-glucopyranosyl)oxy]-14,21-epoxy-21-hydroxy-(3$\beta$,5$\beta$,14$\beta$,20S,21S)-24-nor-cholanic acid lactone in 60% yield.

455 mg of the aforementioned protected glycoside were dissolved in 60 ml of 0.05N potassium hydroxide in methanol-water 99:1. After 72 h at r.t., the solution is concentrated to dryness, the residue dissolved in water and the resulting solution acidified at pH 5 with acetic acid. The resulting precipitate was filtered, washed with distilled water and dried to give 232 mg of the title compound in 80% yield.

EXAMPLE 2

3-[(3-amino-3-deoxy-$\beta$-D-glucopyranosyl)oxy]-14,21-epoxy-21-hydroxy-(3$\beta$,5$\beta$,14$\beta$,20S,21S)-24-nor-cholanic acid lactone 553 mg of 3-[(3-amino-3-deoxy-$\beta$-D-glucopyranosyl)oxy]-14,21-epoxy-21-hydroxy-3$\beta$,5$\beta$,14$\beta$,20S,21R)-24-nor-cholanic acid were suspended in 140 ml of distilled water and brought into solution acidifying at pH 1 with 1N hydrochloric acid. After 3 h at r.t. the mixture was brought to pH 8 by addition of a saturated sodium hydrogen carbonate solution and extracted with chloroform-methanol 8:2. The organic layer was washed with a saturated sodium chloride solution, dried over anhydrous sodium sulfate, evaporated to dryness and crystallized from absolute ethyl alcohol to give 428 mg of the title compounds in 80% yield, m.p. 285°–288° C. (dec.).

EXAMPLE 3

3-[(3-amino-3-deoxy-$\beta$-D-allopyranosyl)oxy]-14,21-epoxy-21-hydroxy-(3$\beta$,5$\beta$,14$\beta$,20S,21R)-24-nor-cholanic acid Operating as in Example 1 but employing 3-deoxy-2,4,6-tri-O-acetyl-3-trifluoroacetamido-$\alpha$-D-allopyranosyl bromide, the title compound was obtained in 37% yield.

EXAMPLE 4

3-[(3-amino-3-deoxy-$\beta$-D-allopyranosyl)oxy]-14,21-epoxy-21-hydroxy-(3$\beta$,5$\beta$,14$\beta$,20S,21S)-24-nor-cholanic acid lactone Operating as in Example 2 but employing 3-[(3-amino-3-deoxy-$\beta$-D-allopyranosyl)oxy]-14,21-epoxy-21-hydroxy-(3$\beta$,5$\beta$,14$\beta$,20S,21R)-24-nor-cholanic acid, the title compound was obtained in 77% yield, m.p. 244°–246° C.

EXAMPLE 5

3-[(3-deoxy-3-dimethylamino-$\beta$-D-glucopyranosyl)oxy]-14,21-epoxy-21-hydroxy-(3$\beta$,5$\beta$,14$\beta$,20S,21R)-24-nor-cholanic acid Operating as in Example 1 but employing 3-deoxy-3-dimethylamino-2,4,6-tri-O-acetyl-$\alpha$-D-glucopyranosyl bromide, the title compound was obtained in 45% yield.

EXAMPLE 6

3-[(3-deoxy-3-dimethylamino-$\beta$-D-glucopyranosyl)oxy]-14,21-epoxy-21-hydroxy-(3$\beta$,5$\beta$,14$\beta$,20S,21S)-24-nor cholanic acid lactone Operating as in Example 2 but employing 3-[(3-deoxy-3-dimethylamino-$\beta$-D-glucopyranosyl)oxy]-14,21-epoxy-21-hydroxy-(3$\beta$,5$\beta$,14$\beta$,20S,21R)-24-nor-cholanic acid, the title compound was obtained in 75% yield.

EXAMPLE 7

3-[(2-amino-2-deoxy-$\beta$-D-glucopyranosyl)-oxy]-14,21-epoxy-21-hydroxy-(3$\beta$,5$\beta$,14$\beta$,20S,21R)-24-nor-cholanic acid Operating as in Example 1 but employing 2-deoxy-3,4-6-tri-O-acetyl-2-trifluoroacetamido-$\alpha$-D-glucopyranosyl bromide, the title compound was obtained in 40% yield.

EXAMPLE 8

3-[(2-amino-2-deoxy-$\beta$-D-glucopyranosyl)oxy]-14,21-epoxy-21-hydroxy-(3$\beta$,5$\beta$,14$\beta$,20S,21S)-24-nor-cholanic acid lactone Operating as in Example 2 but employing 3-[(2-amino-2-deoxy-$\beta$-D-glucopyranosyl)oxy]-14,21-epoxy-21-hydroxy-(3$\beta$,5$\beta$,14$\beta$,20S,21R)-24-nor cholanic acid, the title compound was obtained in 73% yield.

EXAMPLE 9

3-[(3-amino-3-deoxy-$\beta$-L-glucopyranosyl)oxy]-14,21-epoxy-21-hydroxy-(3$\beta$,5$\beta$,14$\beta$,20S,21R)-24-nor-cholanic acid Operating as in Example 1 but employing 3-deoxy-2,4,6-tri-O-acetyl-3-trifluoroacetamido-$\alpha$-L-glucopyranosyl bromide, the title compound was obtained in 50% yield.

EXAMPLE 10

3-[(3-amino-3-deoxy-$\beta$-L-glucopyranosyl)oxy]-14,21-epoxy-21-hydroxy-(3$\beta$,5$\beta$,14$\beta$,20S,21S)-24-nor-cholanic acid lactone Operating as in Example 2 but employing 3-[(3-amino-3-deoxy-$\beta$-L-glucopyranosyl)oxy]-14,21-epoxy-21-hydroxy-(3$\beta$,5$\beta$,14$\beta$,20S,21R)-24-nor-cholanic acid, the title compound was obtained in 83% yield.

EXAMPLE 11

3-[(3-amino-3-deoxy-$\beta$-L-allopyranosyl)oxy]-14,21-epoxy-21-hydroxy-(3$\beta$,5$\beta$,14$\beta$,20S,21R)-24-nor-cholanic acid Operating as in Example 1 but employing 3-deoxy-2,4,6-tri-O-acetyl-3-trifluoroacetamico-$\alpha$-L-allopyranosyl bromide, the title compound was obtained in 35% yield.

EXAMPLE 12

3-[(3-amino-3-deoxy:$\beta$-L-allopyranosyl)oxy]-14,21-epoxy-21-hydroxy-(3$\beta$,5$\beta$,14$\beta$,20S,21S)-24-nor-cholanic acid lactone Operating as in Example 2 but employing 3-[(3-amino-3-deoxy-$\beta$-allopyranosyl)oxy]-14,21-epoxy-21-hydroxy-(3$\beta$,5$\beta$,14$\beta$,20S,21R)-24-nor-cholanic acid, the title compound was obtained in 75% yield.

EXAMPLE 13

3-[(3-amino-2,3,6-trideoxy-$\alpha$-L-lyxo-hexopyranosyl)oxy]-14,21-epoxy-21-hydroxy-(3$\beta$,5$\beta$,14$\beta$,20S,21R)-24-nor-cholanic acid Operating as in Example 1 but employing 2,3,6-trideoxy-3-trifluoroacetamido-4-O-trifluoroacetyl-$\alpha$-L-lyxo-hexopyranosyl chloride, a mixture of $\alpha$ and $\beta$-glycosides was obtained in 62% yield.

By crystallization, the title compound was obtained in 30% yield.

EXAMPLE 14

3-[(3-amino-2,3,6-trideoxy-$\alpha$-L-lyxo-hexopyranosyl)oxy]-14,21-epoxy-21-hydroxy-(3$\beta$,5$\beta$,14$\beta$,20S,21S)-24-nor-cholanic acid lactone Operating as in Example 2 but employing 3-[(3-amino-2,3,6-trideoxy-$\alpha$-L-lyxo-hexopyranosyl)oxy]-14,21-epoxy-21-hydroxy-(3$\beta$,5$\beta$,14$\beta$,20S,21R)-24-nor-cholanic acid, the title compound was obtained in 58% yield, m.p. 240°–243° C.

EXAMPLE 15

3-[(3-amino-2,3,6-trideoxy-$\beta$-L-lyxo-hexopyranosyl)oxy]-14,21-epoxy-21-hydroxy-(3$\beta$,5$\beta$,14$\beta$,20S,21R)-24-nor-cholanic acid The residue of the mother liquors obtained in Example 13, was crystallized giving the title compound in 23% yield.

EXAMPLE 16

3-[(3-amino-2,3,6-trideoxy-β-L-lyxo-hexopyranosyl)oxy]-14,21-epoxy-21-hydroxy-(3β,5β,14β,20S,21S)-24-nor-cholanic acid lactone Operating as in Example 2 but employing 3-[(3-amino-2,3,6-trideoxy-β-L-lyxo-hexopyranosyl)oxy]-14,21-epoxy-21-hydroxy-(3β,5β,14β,20S,21R)-24-nor-cholanic acid, the title compound was obtained in 65% yield.

EXAMPLE 17

3-[(3-amino-2,3,6-trideoxy-α-D-lyxo-hexopyranosyl)oxy]-14,21-epoxy-21-hydroxy-(3β,5β,14β,20S,21R)-24-nor-cholanic acid Operating as in Example 1 but employing 2,3,6-trideoxy-3-trifluoroacetamido-4-O-trifluoroacetyl-α-D-lyxo-hexopyranosyl chloride a mixture of α and β-glycosides was obtained in 54% yield.

The title compound was obtained by crystallization in 28% yield.

EXAMPLE 18

3-[(3-amino-2,3,6-trideoxy-α-D-lyxo-hexopyranosyl)oxy]-14,21-epoxy-21-hydroxy-(3β,5β,14β,20S,21S)-24-nor-cholanic acid lactone Operating as in Example 2 but employing 3-[(3-amino-2,3,6-trideoxy-α-D-lyxo-hexopyranosyl)oxy]-14,21-epoxy-21-hydroxy-(3β,5β,14β,20S,21R)-24-nor-cholanic acid, the title compound was obtained in 73% yield.

EXAMPLE 19

3-[(3-amino-2,3,6-trideoxy-β-D-lyxo-hexopyranosyl)oxy]-14,21-epoxy-21-hydroxy-(3β,5β,14β,20S,21R)-24-nor-cholanic acid The residue of the mother liquors obtained in Example 17, was crystallized giving the title compound in 19% yield.

EXAMPLE 20

3-[(3-amino-2,3,6-trideoxy-β-D-lyxo-hexopyranosyl)oxy]-14,21-epoxy-21-hydroxy-(3β,5β,14β,20S,21S)-24-nor-cholanic acid lactone Operating as in Example 2 but employing 3-[(3-amino-2,3,6-trideoxy-β-D-lyxo-hexopyranosyl)oxy]-14,21-epoxy-21-hydroxy-(3β,5β,14β,20S,21R)-24-nor-cholanic acid, the title compound was obtained in 76% yield.

EXAMPLE 21

3-[(3-amino-2,3,6-trideoxy-α-L-arabino-hexopyranosyl)oxy]-14,21-epoxy-21-hydroxy-(3β,5β,14β,20S,21R)-24-nor-cholanic acid Operating as in Example 1 but employing 2,3,6-trideoxy-3-trifluoroacetamido-4-O-trifluoroacetyl-α-L-arabino-hexopyranosylchloride, a mixture of α and β-glycosides was obtained in 70% yield. The title compound was obtained by crystallization in 36% yield.

EXAMPLE 22

3-[(3-amino-2,3,6-trideoxy-α-L-arabino-hexopyranosyl)oxy]-14,21-epoxy-21-hydroxy-(3β,5β,14β,20S,21S)-24-nor-cholanic acid lactone Operating as in Example 2 but employing 3-[(3-amino-2,3,6-trideoxy-α-L-arabino-hexopyraosyl)oxy]-14,21-epoxy-21-hydroxy-(3β,5β,14β,20S,21R)-24-nor-cholanic acid, the title compound was obtained in 75% yield.

EXAMPLE 23

3-[(3-amino-2,3,6-trideoxy-β-L-arabino-hexopyranosyl)oxy]-14,2'-epoxy-21-hydroxy-(3β,5β,14β,20S,21R)-24-nor-cholanic acid The residue of the mother liquors obtained in Example 21, was crystallized giving the title compound in 28% yield.

EXAMPLE 24

3-[(3-amino-2,3,6-trideoxy-β-L-arabino-hexopyranosyl)oxy]-14,21-epoxy-21-hydroxy-(3β,5β,14β,20S,21S)-24-nor-cholanic acid lactone Operating as in Example 2 but employing 3-[(3-amino-2,3,6-trideoxy-β-L-arabino-hexopyranosyl)oxy]-14,21-epoxy-21-hydroxy-(3β,5β,14β,20S,21R)-24-nor-cholanic acid, the title compound was obtained in 76% yield.

EXAMPLE 25

3-[(3-amino-2,3,6-trideoxy-α-D-arabino-hexopyranosyl)oxy]-14,21-epoxy-21-hydroxy-(3β,5β,14β,20S,21R)-24-nor-cholanic acid Operating as in Example 1 but employing 2,3,6-trideoxy-3-trifluoroacetamido-4-O-trifluoroacetyl-α-D-arabino-hexopyranosyl chloride, a mixture of α and β-glycosides was obtained in 56% yield. The title compound was obtained by crystallization in 25% yield.

EXAMPLE 26

3-[(3-amino-2,3,6-trideoxy-α-D-arabino-hexopyranosyl)oxy]-14,21-epoxy-21-hydroxy-(3β,5β,14β,20S,21S)-24-nor-cholanic acid lactone Operating as in Example 2 but employing 3-[(3-amino-2,3,6-trideoxy-α-D-arabino-hexopyranosyl)oxy]-14,21-epoxy-21-hydroxy-(3β,5β,14β,20S,21R)-24-nor-cholanic acid, the title compound was obtained in 72% yield.

EXAMPLE 27

3-[(3-amino-2,3,6-trideoxy-β-D-arabino-hexopyranosyl)oxy]-14,21-epoxy-21-hydroxy-(3β,5β,14β,20S,21R)-24-nor-cholanic acid The residue of the mother liquors obtained in Example 25 was crystallized giving the title compound in 26% yield.

EXAMPLE 28

3-[(3-amino-2,3,6-trideoxy-β-D-arabino-hexopyranosyl)oxy]-14,21-epoxy-21-hydroxy-(3β,5β,14β,20S,21S)-24-nor-cholanic acid lactone Operating as in Example 2 but employing 3-[(3-amino-2,3,6-trideoxy-β-D-arabino-hexopyranosyl)oxy]-14,21-epoxy-21-hydroxy-(3β,5β,14β,20S,21R)-24-nor-cholanic acid, the title compound was obtained in 75% yield.

EXAMPLE 29

3-[(3-amino-3,6-dideoxy-α-L-altropyranosyl)oxy]-14,21-epoxy-21-hydroxy-(3β,5β,14β,20S,21R)-24-nor-cholanic acid Operating as in Example 1, but employing 3,6-dideoxy-2,4-di-O-acetyl-3-trifluoroacetamido-α-L-altropyranosyl bromide, the title compound was obtained in 35% yield.

EXAMPLE 30

3-[(3-amino-3,6-dideoxy-α-L-altropyranosyl)oxy]-14,21-epoxy-21-hydroxy-(3β,5β,14β,20S,21S)-24-nor-cholanic acid lactone Operating as in Example 2, but employing 3-[(3-amino-3,6-dideoxy-α-L-altropyranosyl)oxy]-14,21-epoxy-21-hydroxy-(3β,5β,14β,20S,21R)-24-nor-cholanic acid, the title compound was obtained in 75% yield, m.p. 238°–240° C.

EXAMPLE 31

3-[(3-amino-3,6-dideoxy-α-D-altropyranosyl)oxy]-14,21-epoxy-21-hydroxy-(3β,5β,14β,20S,21R)-24-nor-cholanic acid Operating as in Example 1, but employing 3,6-dideoxy-2,4-di-O-acetyl-3-trifluoroacetamido-α-D-altropyranosyl bromide, the title compound was obtained in 42% yield.

EXAMPLE 32

3-[(3-amino-3,6-dideoxy-α-D-altropyranosyl)oxy]-14,21-epoxy-21-hydroxy-(3β,5β,14β,20S,21S)-24-nor-cholanic acid lactone Operating as in Example 2, but employing 3-[(3-amino-3,6-dideoxy-α-D-altropyranosyl)oxy]-14,21-epoxy-21-hydroxy-(3β,5β,14β,20S,21R)-24-nor-cholanic acid, the title compound was obtained in 76% yield, m.p. 255°–257° C.

EXAMPLE 33

3-[(3,6-dideoxy-3-dimethylamino-α-L-altropyranosyl)oxy]-14,21-epoxy-21-hydroxy-(3β,5β,14β,20S,21R)-24-nor-cholanic acid Operating as in Example 1, but employing 3,6-dideoxy-3-dimethylamino-2,4-di-O-acetyl-α-L-altropyranosyl bromide hydrobromide, the title compound was obtained in 38% yield.

EXAMPLE 34

3-[(3,6-dideoxy-3-dimethylamino-α-L-altropyranosyl)oxy]-14,21-epoxy-21-hydroxy-(3β,5β,14β,20S,21S)-24-nor-cholanic acid lactone Operating as in Example 2, but employing 3-[(3,6-dideoxy-3-dimethylamino-α-L-altropyranosyl)oxy]-14,21-epoxy-21-hydroxy-(3β,5β,14β,20S,21R)-24-nor-cholanic acid, the title compound was obtained in 75% yield.

EXAMPLE 35

3-[(3,6-dideoxy-3-dimethylamino-α-L-altropyranosyl)oxy]-14,21-epoxy-21-hydroxy-(3β,5β,14β,20S,21R)-24-nor-cholanic acid Operating as in Example 1, but employing 3,6-dideoxy-3-dimethylamino-2,4-di-O-acetyl-α-D-altropyranosyl bromide hydrobromide, the title compound was obtained in 33% yield.

EXAMPLE 36

3-[(3,6-dideoxy-3-dimethylamino-α-L-altropyranosyl)oxy]-14,21-epoxy-21-hydroxy-(3β,5β,14β,20S,21S)-24-nor-cholanic acid lactone Operating as in Example 2, but employing 3-[(3,6-dideoxy-3-dimethylamino-α-L-altropyranosyl)oxy]-14,21-epoxy-21-hydroxy-(3β,5β,14β,20S,21R)-24-nor-cholanic acid, the title compound was obtained in 70% yield.

EXAMPLE 37

3-[(3-amino-3-deoxy-α-D-mannopyranosyl)-oxy]-14,21-epoxy-21-hydroxy-(3β,5β,14β,20S,21R)-24-nor-cholanic acid Operating as in Example 1, but employing 3-deoxy-3,4,6-tri-O-acetyl-3-trifluoroacetamido-α-D-mannopyranosyl bromide, the title compound was obtained in 42% yield.

EXAMPLE 38

3-[(3-amino-3-deoxy-α-D-mannopyranosyl)-oxy]-14,21-epoxy-21-hydroxy-(3β,5β,14β,20S,21S)-24-nor-cholanic acid lactone Operating as in Example 2, but employing 3-[(3-amino-3-deoxy-α-D-mannopyranosyl)-oxy]-14,21-epoxy-21-hydroxy-(3β,5β,14β,20S,21R)-24-nor-cholanic acid, the title compound was obtained in 78% yield.

EXAMPLE 39

3-[(3-amino-3,6-dideoxy-α-D-mannopyranosyl)-oxy]-14,21-epoxy-21-hydroxy-(3β,5β,14β,20S,21R)-24-nor-cholanic acid Operating as in Example 1, but employing 2,4-di-O-acetyl-3,6-dideoxy-3-trifluoroacetamido-α-D-mannopyranosyl bromide, the title compound was obtained in 45% yield.

EXAMPLE 40

3-[(3-amino-3,6-dideoxy-α-D-mannopyranosyl)-oxy]-14,21-epoxy-21-hydroxy-(3β,5β,14β,20S,21S)-24-nor-cholanic lactone Operating as in Example 2, but employing 3-[(3-amino-3,6-dideoxy-α-D-mannopyranosyl)-oxy]-14,21-epoxy-21-hydroxy-(3β,5β,14β,20S,21R)-24-nor-cholanic acid, the title compound was obtained in 75% yield.

EXAMPLE 41

3-[(3-amino-3-deoxy-α-L-mannopyranosyl)-oxy]-14,21-epoxy-21-hydroxy-(3β,5β,14β,20S,21R)-24-nor-cholanic acid Operating as in Example 1, but employing 3-deoxy-2,4,6-tri-O-acetyl-3-trifluoroacetamido-α-L-mannopyranosyl bromide, the title compound was obtained in 48% yield.

EXAMPLE 42

3-[(3-amino-3-deoxy-α-L-mannopyranosyl)-oxy]-14,21-epoxy-21-hydroxy-(3β,5β,14β,20S,21S)-24-nor-cholanic acid lactone Operating as in Example 2, but employing [3-[(3-amino-3-deoxy-α-L-mannopyranosyl)-oxy]-14,21-epoxy-21-hydroxy-(3β,5β,14β,20S,21R)-24-nor-cholanic acid, title compound was obtained in 75% yield.

EXAMPLE 43

3-[(3-amino-3,6-dideoxy-α-L-mannopyranosyl)-oxy]-14,21-epoxy-21-hydroxy-(3β,5β,14β,20S,21R)-24-nor-cholanic acid Operating as in Example 1, but employing 2,4-di-O-acetyl-3,6-dideoxy-3-trifluoroacetamido-α-L-mannopyranosyl bromide, the title compound was obtained in 46% yield.

EXAMPLE 44

3-[(3-amino-3,6-dideoxy-α-L-mannopyranosyl)-oxy]-14,21-epoxy-21-hydroxy-(3β,5β,14β,20S,21S)-24-nor-cholanic acid lactone Operating as in Example 2, but employing 3-[(3-amino-3,6-dideoxy-α-L-mannopyranosyl)-oxy]-14,21-epoxy-21-hydroxy-(3β,5β,14β,20S,21R)-24-nor-cholanic acid the title compound was obtained in 80% yield.

EXAMPLE 45

3-[(3-amino-3-deoxy-2-D-allopyranosyl)oxy]-14,21-epoxy-21-hydroxy-(3β,5β,14β,20S,21S)-24-nor-cholanic acid lactone Operating as in Example 1, but employing 3-deoxy-3-trifluoroacetamido-2,4,6-tri-O-acetyl-α-D-allopyranosyl-bromide, the title compound was obtained in 29% yield, m.p. 258°–260° C.

The invention is illustrated further in the below formulation examples:

Formulation 1

| Ingredient | Part |
|---|---|
| compound of the formula (I) | 45 |
| starch | 10 |
| lactose | 45 |

The ingredients are mixed thoroughly, and tablets or capsules are formulated from the mixture.

Formulation 2

| Ingredient | Part |
|---|---|
| compound of the formula (I) | 10 |
| lactose | 75 |
| magnesium oxide (MgO > 96%) | 15 |

The above ingredients are mixed thoroughly, and powders or fine granules are formed from the mixture.

Formulation 3

| Ingredient | Part |
|---|---|
| compound of the formula (I) | 1 |
| surface active agent | 1 |
| physiological saline | 98 |

The above ingredients are mixed under warming, and dispensed under sterile conditions into ampoules for use as injections.

We claim:

1. A compound having the general formula I

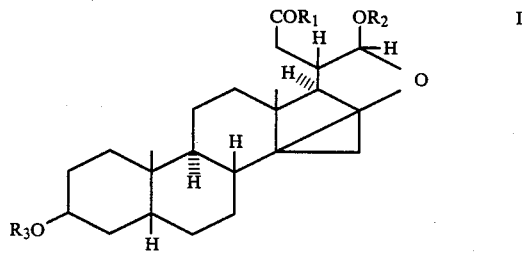

wherein either $R_1$ represents a hydroxy group or an alkoxy group having from 1 to 4 carbon atoms and $R_2$ represents a hydrogen atom or an alkyl group having from 1 to 4 carbon atoms, or $R_1$ and $R_2$ taken together represent a chemical bond; and $R_3$ represents an aminodeoxy or aminodideoxy or aminotrideoxy sugar residue of the D or L series, or a pharmaceutically acceptable salt thereof.

2. A compound according to claim 1 wherein the sugar residue is alkyl-substituted.

3. A compound according to claim 1 wherein said sugar residue is a 2-amino or 2-alkylamino-2-deoxy-hexopyranosyl, 3-amino or 3-alkylamino-3-deoxy-hexopyranosyl, 3-amino or 3-alkylamino-3,6-dideoxy-hexopyranosyl or 3-amino or 3-alkylamino-2,3,6-trideoxy-hexopyranosyl or 4-amino or 4-alkylamino-2,4,6-trideoxy-hexopyranosyl.

4. A compound according to claim 1 wherein $R_2$ represents a methyl, ethyl, propyl or butyl group or hydrogen atom and $R_1$ represents a hydroxy, ethoxy, propoxy, methoxy or butoxy group.

5. A pharmaceutical composition comprising an effective amount of a compound having the general formula I as defined in claim 1 or a pharmaceutically acceptable salt of such a compound in admixture with a pharmaceutically acceptable diluent or carrier.

6. A pharmaceutical composition comprising a compound having the general formula I as defined in claim 1 or a pharmaceutically acceptable salt of such a compound in an amount suitable for administration for the effective treatment of hypertension in admixture with a pharmaceutically acceptable diluent or carrier in an amount suitable for rendering the composition pharmaceutically administrable.

7. A process for treating hypertension comprising administering a compound having the general formula I as defined in claim 1 or the salts thereof in amount effective to reduce hypertension.

* * * * *

UNITED STATES PATENT AND TRADEMARK OFFICE
CERTIFICATE OF CORRECTION

PATENT NO. : 4,882,315

DATED : November 21, 1989

INVENTOR(S) : Laura Chiodini et al

It is certified that error appears in the above-identified patent and that said Letters Patent is hereby corrected as shown below:

Col. 2, l. 3-4, there should be a line drawn down under the "H"

Col. 2, l. 50, should read "(Na+-K+)-ATPase

Col. 2, l. 67, after "et al" there should be a semi colon

Col. 3, l. 21, correct spelling of word "membrane"

Col. 3, l. 47, should read "Na+"

Col. 3, l. 59, should read "supplied by"

Col. 5, l. 6, take "s" out of word "compound"

Col. 5, l. 10, should read "-allopyranosyl)-oxy"

Col. 5, l. 51, there should be no dash between "glucopyranosyl)oxyl"

Col. 6, l. 31, should read "deoxy-B-L"

Col. 7, l. 68, correct spelling of "hexopyranosyl"

Signed and Sealed this

Eleventh Day of December, 1990

*Attest:*

HARRY F. MANBECK, JR.

*Attesting Officer*      *Commissioner of Patents and Trademarks*